US011529439B2

(12) United States Patent
O'Mahony et al.

(10) Patent No.: US 11,529,439 B2
(45) Date of Patent: Dec. 20, 2022

(54) LUBRICIOUS HYDROPHILIC COATINGS AND METHODS OF FORMING THE SAME

(71) Applicant: Hollister Incorporated, Libertyville, IL (US)

(72) Inventors: John P. O'Mahony, Ardnacrusha (IE); David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 188 days.

(21) Appl. No.: 16/610,264

(22) PCT Filed: May 4, 2018

(86) PCT No.: PCT/US2018/031060
§ 371 (c)(1),
(2) Date: Nov. 1, 2019

(87) PCT Pub. No.: WO2018/204767
PCT Pub. Date: Nov. 8, 2018

(65) Prior Publication Data
US 2020/0147273 A1    May 14, 2020

Related U.S. Application Data

(60) Provisional application No. 62/501,476, filed on May 4, 2017.

(51) Int. Cl.
| | | |
|---|---|---|
| *A61L 29/08* | (2006.01) | |
| *C08L 71/02* | (2006.01) | |
| *C08L 39/06* | (2006.01) | |
| *A61L 29/14* | (2006.01) | |
| *C08K 3/08* | (2006.01) | |
| *C08F 20/06* | (2006.01) | |
| *C08F 20/18* | (2006.01) | |
| *C08K 5/00* | (2006.01) | |
| *C08K 5/07* | (2006.01) | |

(52) U.S. Cl.
CPC .......... *A61L 29/085* (2013.01); *A61L 29/14* (2013.01); *C08F 20/06* (2013.01); *C08F 20/18* (2013.01); *C08K 3/08* (2013.01); *C08K 5/0025* (2013.01); *C08K 5/07* (2013.01); *C08L 39/06* (2013.01); *C08L 71/02* (2013.01); *A61L 2400/10* (2013.01); *A61L 2420/06* (2013.01); *C08K 2003/0812* (2013.01); *C08K 2003/0881* (2013.01); *C08K 2003/0893* (2013.01); *C08L 2312/00* (2013.01)

(58) Field of Classification Search
None
See application file for complete search history.

(56) References Cited

U.S. PATENT DOCUMENTS

| | | | |
|---|---|---|---|
| 4,487,808 A | 12/1984 | Lambert | |
| 4,990,357 A | 2/1991 | Karakelle et al. | |
| 5,179,174 A | 1/1993 | Elton | |
| 5,702,754 A | 12/1997 | Zhong | |
| 5,997,517 A | 12/1999 | Whitbourne | |
| 6,020,071 A | 2/2000 | Watson | |
| 6,110,483 A | 8/2000 | Whitbourne et al. | |
| 7,008,979 B2* | 3/2006 | Schottman | C08K 3/22 523/334 |
| 7,220,491 B2 | 5/2007 | Rouns et al. | |
| 7,314,857 B2* | 1/2008 | Madhyastha | A61L 27/227 514/2.4 |
| 8,137,735 B2 | 3/2012 | Wang et al. | |
| 8,287,890 B2* | 10/2012 | Elton | C08G 18/4833 424/78.17 |
| 8,703,167 B2 | 4/2014 | Glauser et al. | |
| 8,911,764 B2 | 12/2014 | Zhao | |
| 8,998,882 B2 | 4/2015 | Knapp et al. | |
| 9,180,227 B2 | 11/2015 | Ludwig et al. | |
| 2004/0117007 A1 | 6/2004 | Whitbourne et al. | |
| 2008/0193497 A1 | 8/2008 | Samuelsen et al. | |
| 2009/0048537 A1 | 2/2009 | Lydon et al. | |
| 2010/0293994 A1* | 11/2010 | Murayama | C08F 8/42 62/515 |
| 2011/0189377 A1 | 8/2011 | Atanasoska et al. | |
| 2011/0200828 A1 | 8/2011 | Li et al. | |
| 2014/0113070 A1 | 4/2014 | Schumann et al. | |
| 2014/0180261 A1* | 6/2014 | Nyman | A61M 25/0015 427/2.3 |

(Continued)

FOREIGN PATENT DOCUMENTS

| | | |
|---|---|---|
| EP | 0913445 | 5/1999 |
| WO | WO 2008/031601 A1 | 3/2008 |
| WO | 2010/001813 A1 | 1/2010 |
| WO | WO 2015/066227 A1 | 5/2015 |

OTHER PUBLICATIONS

International Search Report and Written Opinion of the International Searching Authority dated Jul. 31, 2018 for International Application No. PCT/US2018/031060.

(Continued)

*Primary Examiner* — Tae H Yoon
(74) *Attorney, Agent, or Firm* — Cook Alex Ltd.

(57) ABSTRACT

Self-crosslinking hydrophilic coatings and methods of forming the same are disclosed. The lubricious hydrophilic coatings may be formed on the surfaces of medical devices. The self-crosslinking hydrophilic coating formulations form a hydrophilic coating when the solvent of the hydrophilic coating formulation is dried off, or otherwise removed, from the formulation.

16 Claims, No Drawings

(56) References Cited

U.S. PATENT DOCUMENTS

2015/0065998 A1* 3/2015 Nielsen ................. A61L 29/085
604/523
2015/0284584 A1* 10/2015 Holguin ................ C08F 220/20
524/833

OTHER PUBLICATIONS

European Office Action dated Feb. 19, 2021 for European Application No. 18726663.0.

* cited by examiner

LUBRICIOUS HYDROPHILIC COATINGS AND METHODS OF FORMING THE SAME

RELATED APPLICATION

The present application is the U.S. National Stage Application of PCT Application No. PCT/US2018/031060, filed May 4, 2018, which claims the benefit of and priority to U.S. Provisional Application No. 62/501,476, filed May 4, 2017, both of which are hereby incorporated herein by reference.

FIELD OF THE DISCLOSURE

The present disclosure is directed to hydrophilic coatings and methods of forming the same. More particularly, the present disclosure is directed to lubricious hydrophilic coatings formed on the surfaces of medical devices. Even more particularly, the present disclosure is directed to hydrophilic coating formulations that self-crosslink to form a hydrophilic coating when the solvent of the hydrophilic coating formulation is dried off, or otherwise removed, from the formulation.

BACKGROUND

It is desirable for medical devices that are inserted into the body to have a lubricated or lubricious outer surface to facilitate insertion into and/or removal of the medical device from the body. Such devices may include, for example, urinary catheters, endoscopes, cardiovascular catheters, syringes, vascular stents, etc. Such medical devices may have a hydrophilic coating or layer disposed on an outer surface thereof. Hydrophilic coatings are becoming the preferred method of providing lubricious surfaces because of their high lubricity and ease of use. Hydrophilic coatings become slippery or lubricious when wetted with a wetting fluid, such as saline or water. The wetted lubricious hydrophilic coating eases insertion and removal of the device, which can result in minimizing soft tissue damage and reducing overall discomfort during use of the medical device.

When a hydrophilically coated medical is used, the hydrophilic coating is typically wetted for a certain period of time prior to use to activate the hydrophilic coating. For example, the user may immerse or otherwise contact the hydrophilic coating with a wetting fluid to wet or activate the coating. In some instances, the medical device is packaged in a packaging that includes liquid or vapor water within the package that hydrates the coating while the device is in the package so that the device is ready to use right out of the package.

Hydrophilic coatings are oftentimes formed on the surfaces of medical devices by a dip coating process that includes dipping the medical device into a hydrophilic coating formulation. The formulation generally includes a solvent, one or more hydrophilic polymers and additives. After the hydrophilic coating formulation has been applied to the surface of the medical device, the coating formulation is cured to form a hydrophilic coating on the surface of the medical device. It is commonplace for the coating formulation to include a photo activated crosslinker and to utilize a radiation or photo curing process to cure the coating formulation. One of the more widely used curing processes is ultraviolet (UV) curing wherein the coating formulation is exposed to UV light, which activates the crosslinker to commence crosslinking of the polymer within the coating formulation to thereby form the hydrophilic coating.

While UV curing is widely used, it is not without its issues. For example, UV curing can require considerable time to achieve the desired degree of crosslinking, which can reduce manufacturing efficiency. Additionally, the materials being crosslinked can be highly sensitive to the UV dose, which can vary as UV lamps degrade over time. This may lead to variations of the level of crosslinking and to under crosslinking of the coating.

Therefore, there remains a need for improved curing/crosslinking processes for forming hydrophilic coatings.

SUMMARY

In one aspect, a hydrophilically coated medical device that includes a medical device having a surface and a hydrophilic coating disposed on the surface of the medical device. The hydrophilic coating including a hydrophilic polymer and metal.

In another aspect, a hydrophilically coated medical device that includes a medical device having a surface and a hydrophilic coating disposed on the surface of the medical device. The hydrophilic coating comprising a hydrophilic polymer and by-products of a metal chelating crosslinker.

In yet another aspect, a formulation for forming a hydrophilic coating that includes a hydrophilic polymer, a metal chelating crosslinker, and a solvent.

In yet a further aspect, a method for forming a hydrophilic coating on a medical device that includes applying a hydrophilic coating formulation to a surface of the medical device wherein the hydrophilic coating formation includes a hydrophilic polymer, a metal chelating crosslinker and a solvent that suppresses crosslinking. The method further includes drying off the solvent of the hydrophilic coating formulation to promote or initiate crosslinking, and thereby forming the hydrophilic coating on the surface of the medical device.

DETAILED DESCRIPTION OF THE EMBODIMENTS

The present disclosure is directed to methods of forming hydrophilic coatings, and more particularly lubricious hydrophilic coatings, on the surface of a substrate, such as a medical device. The methods include applying a hydrophilic coating formulation to the surface of the substrate wherein the hydrophilic coating formulation includes a hydrophilic polymer, a crosslinker to crosslink the hydrophilic polymer and a blocking solvent, which may be a volatile stabilizer or may include a volatile stabilizer, that suppresses or blocks the crosslinking reaction. In one embodiment, the solvent may be a single solvent that is a blocking solvent or volatile stabilizer. In another embodiment, the solvent may include 30 wt % or more of a blocking or volatile stabilizing solvent and the remainder a solution, reaction or carrier solvent. After the hydrophilic coating formulation is applied to the surface of the medical device, the blocking solvent is driven, dried off (e.g. evaporated) or otherwise removed. With the solvent driven off, the crosslinker is active and free to start crosslinking reactions, thereby curing the hydrophilic coating formulation and forming the crosslinked hydrophilic coating. The present disclosure is also directed to the hydrophilic coatings formed from such methods and the hydrophilic coating formulations that are employed to form the hydrophilic coatings on a medical device.

As used herein, the term "hydrophilic coating" means a coating disposed on a surface of a substrate wherein the coating has hydrophilic properties, and preferably becomes highly lubricious when wetted with a wetting fluid. The terms "hydrophilic coating formulation" and "coating formulation" refer to a solution or dispersion that includes the components for forming a hydrophilic coating and that is applied to the surface of a substrate and is dried to form a hydrophilic coating.

The methods of forming hydrophilic coatings of the present disclosure may include applying a hydrophilic coating formulation directly on the surface of a substrate, such as a medical device, and then drying the hydrophilic coating formulation to crosslink the hydrophilic polymer and form a hydrophilic coating on the surface of the substrate. In other embodiments, the methods may include the use of a base coat formulation and a top coat formation wherein a base coat formulation is applied to the surface of a substrate to form a base coat on the surface of the substrate, and then a top coat formulation is applied over the base formulation to form the hydrophilic coating. The base coat may have suitable adhesion/attraction to both the surface of the substrate and the top coat such that the base coat serves as a tie-layer or binding layer.

The hydrophilic coating formulations (including the base coat and top coat formulations) disclosed herein, the hydrophilic coatings formed therefrom and the methods of forming such hydrophilic coatings are particularly useful in the field of urinary catheters. However, the formulations, coatings and methods may be used to coat virtually any medical device for which it is desired to provide a hydrophilic coating on the surface thereof. The formulations, coatings and methods are particularly useful for medical devices that are intended to be inserted into and removed from the body, such as urinary catheters, endoscopes, drainage catheters, etc.

When the methods include the use of base coat formulations and top coat formulations to form the hydrophilic coating, the base and top coat formulations disclosed herein may be used with one another to form a lubricious hydrophilic coating on a substrate. While the base coat and top coat formulations may be used with each other to form hydrophilic coatings, such base and top coat formulations are not required to be used with each other. That is, the base coat formulations disclosed herein may not only be used with the top coat formulations disclosed herein but may also be used with other suitable top coat formulations to form a hydrophilic coating on a medical device. Similarly, the top coat formulations disclosed herein may not only be used with the base coat formulations disclosed herein but may also be used with other suitable base coat formulations to form a hydrophilic coating on the surface of a medical device. Furthermore, as mentioned above the top coat formulations or hydrophilic coating formulations may be applied directly to the surface of the substrate to form a hydrophilic coating on the substrate without the use of a base coat.

The hydrophilic coating formulations (including base and top coat formulations) may include a hydrophilic polymer, chelating metal crosslinker and a blocking solvent. The hydrophilic polymer may be any suitable hydrophilic polymer in which crosslinking of the polymer can be initiated or carried out by a chelating metal crosslinker. In one embodiment, the hydrophilic polymer includes a copolymer of the hydrophilic polymer and an acid or hydroxyl function monomer. For example, the hydrophilic polymer may be a copolymer of a hydrophilic polymer and an acid group such as carboxylic acid. The carboxylic acid may include but is not limited to acrylic acid and methacrylic acid. In another example, the hydrophilic polymer may be a copolymer of the hydrophilic polymer and a hydroxyl function monomer, such as but not limited hydroxyethylacrylate and/or hydroxyethylmethacrylate. The hydrophilic polymer may include but is not limited to polyvinylpyrrolidone (PVP) or polyethylene oxide (POE).

The metal chelating crosslinker may be a metal-acetylacetonate crosslinker wherein the metal is titanium, aluminum, zinc, or any other metal suitable for medical use. For example, the crosslinker may have formula of:

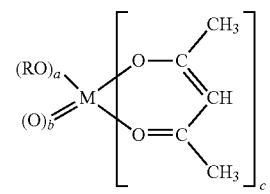

M—central metal atom
a + b + c = n-metal valence
b = 0 or 1
R = alkyl group

The solvent may be a crosslink suppressing, blocking or volatile stabilizing solvent that renders the crosslinking reaction between the hydrophilic polymer and the metal chelating crosslinker inactive. The solvent may be such a blocking solvent or the solvent may be a mixture of solvents wherein one of the solvents is such a blocking solvent. Such blocking solvents may include 2, 4 pentanedione or isopropyl alcohol. Accordingly, the solvent may be a mixture that includes 2, 4 pentanedione and/or isopropyl alcohol, along with another solvent. The formulation also may include additives, such as plasticizer, osmolality increase agent and antioxidant.

In one exemplary hydrophilic coating formulation, the formulation may include the solvent in an amount of between about 50 weight percent (wt %) and about 98 wt %, hydrophilic polymer in an amount between about 1.95 wt % and about 48.5 wt %, and a metal chelating crosslinker in amount between about 0.05 wt % and about 1.5 wt %. In one embodiment, the formulation includes isopropyl alcohol as the solvent and volatile stabilizer, poly (N-vinylpyrrolidone-co-acrylic acid) as the hydrophilic polymer and Titanium acetylacetonate (TiACA) as the metal chelating crosslinker, for example $Ti(C_5H_7O_2)_2(C_3H_7O)_2$.

In one method of forming a hydrophilic coating, a hydrophilic coating formulation is applied directly to a surface of a substrate. The hydrophilic coating formulation may be applied by, for example, dip coating, spraying or brushing. The hydrophilic coating formulation includes a hydrophilic polymer, a metal chelating crosslinker, a blocking solvent and, optionally, additives. After the hydrophilic coating formulation has been applied to the surface, the blocking solvent is dried off leaving the metal chelating crosslinker reactive and free to commence crosslinking reactions to crosslink the hydrophilic polymer, thereby crosslinking the polymer and forming a hydrophilic coating on the surface of the substrate. The blocking solvent may be dried or driven off by heating the hydrophilic coating formulation. In some embodiments, the crosslinking process will continue even after the heat is removed and while the solvent continues to dry off of the hydrophilic coating formulation/hydrophilic coating.

In another method of forming a hydrophilic coating, a base hydrophilic coating formulation including a hydrophilic polymer, a metal chelating crosslinker and a blocking solvent is applied to the surface of the substrate and the blocking solvent is dried off to crosslink the hydrophilic polymer, thereby forming a base coat. A top hydrophilic coating formulation including a hydrophilic polymer, a metal chelating crosslinker and a blocking solvent is applied over the base coat and the blocking solvent is dried off to crosslink the hydrophilic polymer of the top coat formulation, thereby forming a hydrophilic coating.

The hydrophilic coatings disclosed herein are preferably coatings that become lubricious when wetted with a wetting agent, such as water. The hydrophilic coating may include a crosslinked hydrophilic polymer, by-products of the metal chelating crosslinking and, optionally, additives. For example, the hydrophilic coating may include a crosslinked hydrophilic polymer and a metal. In one embodiment, the metal is bonded to the hydrophilic polymer which may aid in reducing the level of leachables from the hydrophilic coating.

There are advantages that may be obtained from the methods, formulations and coatings disclosed herein. For example, the need for radiation/photo curing may be reduced or eliminated, which may result in shorter and more efficient manufacturing times. The level of crosslinking and the ability to reproduce consistency in the level of crosslinking can be improved through varying the stoichiometric ratios of the hydrophilic polymer and the crosslinking agent.

It should be understood that various changes and modifications to the presently preferred embodiments described herein will be apparent to those skilled in the art. Such changes and modification can be made without departing from the spirit and scope of the invention disclosed herein.

What is claimed is:

1. A hydrophilically coated urinary catheter, comprising:
   a urinary catheter having a surface; and
   a lubricious hydrophilic coating disposed on the surface of the urinary catheter, the hydrophilic coating comprising:
   (i.) a hydrophilic polymer consisting of a copolymer of polyvinylpyrrolidone and an acid or hydroxyl function monomer cross-linked by a metal acetylacetonate crosslinker and
   (ii.) by-products of a metal acetylacetonate crosslinker.

2. The urinary catheter of claim 1 wherein the metal comprises one or more of titanium, aluminum, zinc, and any other suitable metal.

3. The urinary catheter of claim 1 wherein the acid or hydroxyl function monomer comprises a carboxylic acid functional group.

4. The urinary catheter of claim 3 wherein the carboxylic acid is acrylic acid or methacrylic acid.

5. The urinary catheter of claim 1 wherein the acid or hydroxyl function monomer comprises a monomer having a functional hydroxyl group.

6. The urinary catheter of claim 5 wherein the monomer comprises hydroxyethylacrylate and/or hydroxyethylmethacrylate.

7. A hydrophilically coated urinary catheter, comprising:
   a urinary catheter having a surface; and
   a lubricious hydrophilic coating disposed on the surface of the urinary catheter, the hydrophilic coating comprising:
   (i) a hydrophilic polymer consisting of a copolymer of polyvinylpyrrolidone and an acid or hydroxyl function monomer and
   (ii) by-products of a metal acetylacetonate crosslinker.

8. The urinary catheter of claim 7 wherein the by-product of the metal chelating crosslinker comprises acetylacetonate.

9. The urinary catheter of claim 7 wherein the by-product of the metal chelating crosslinker comprises a metal.

10. The urinary catheter of claim 9 wherein the metal comprises one or more of titanium, aluminum, zinc, and any other suitable metal.

11. The urinary catheter of claim 7 wherein acid or hydroxyl function monomer comprises a carboxylic acid.

12. The urinary catheter of claim 11 wherein the carboxylic acid is acrylic acid or methacrylic acid.

13. The urinary catheter of claim 7 wherein the acid or hydroxyl function monomer comprises a monomer having a functional hydroxyl group.

14. The urinary catheter of claim 13 wherein the monomer comprises hydroxyethylacrylate and/or hydroxyethylmethacrylate.

15. The urinary catheter of claim 1 wherein the hydrophilic polymer is poly (N-vinylpyrrolidone-co-acrylic acid).

16. The urinary catheter of claim 7, wherein the hydrophilic polymer is poly (N-vinylpyrrolidone-co-acrylic acid).

\* \* \* \* \*